(12) United States Patent
Bertini et al.

(10) Patent No.: US 9,957,239 B2
(45) Date of Patent: May 1, 2018

(54) PROCESS AND PLANT FOR THE SYNTHESIS OF UREA AND MELAMINE

(71) Applicant: Casale SA, Lugano (CH)

(72) Inventors: Paolo Bertini, Lugano (CH); Gabriele Di Carlo, Lugano (CH)

(73) Assignee: Casale SA, Lugano (CH)

( * ) Notice: Subject to any disclaimer, the term of this patent is extended or adjusted under 35 U.S.C. 154(b) by 0 days. days.

(21) Appl. No.: 15/126,212

(22) PCT Filed: Apr. 16, 2015

(86) PCT No.: PCT/EP2015/058292
§ 371 (c)(1),
(2) Date: Sep. 14, 2016

(87) PCT Pub. No.: WO2015/165741
PCT Pub. Date: Nov. 5, 2015

(65) Prior Publication Data
US 2017/0081297 A1 Mar. 23, 2017

(30) Foreign Application Priority Data
Apr. 28, 2014 (EP) .................................. 14166190

(51) Int. Cl.
| | |
|---|---|
| *C07D 251/60* | (2006.01) |
| *C07D 251/62* | (2006.01) |
| *B01J 3/04* | (2006.01) |
| *B01J 19/24* | (2006.01) |
| *B01J 4/02* | (2006.01) |
| *B01J 10/00* | (2006.01) |
| *C07C 273/12* | (2006.01) |

(52) U.S. Cl.
CPC .............. *C07D 251/60* (2013.01); *B01J 3/04* (2013.01); *B01J 4/02* (2013.01); *B01J 10/00* (2013.01); *B01J 19/24* (2013.01); *C07C 273/12* (2013.01); *Y02P 20/125* (2015.11)

(58) Field of Classification Search
CPC .. C07D 251/60; C07D 251/62; C07C 273/12; B01J 10/00; B01J 19/24; B01J 4/02
USPC .................................................. 544/201, 203
See application file for complete search history.

(56) References Cited

U.S. PATENT DOCUMENTS 6,114,579 A * 9/2000 Van Wijck ............ C07C 273/12
544/201

FOREIGN PATENT DOCUMENTS

| EP | 1 449 827 A1 | 8/2004 |
| WO | 98/08808 A1 | 3/1998 |

OTHER PUBLICATIONS

International Search Report issued in connection with PCT/EP2015/058292.
International Preliminary Report on Patentability issued in connection with PCT/EP2015/058292.

* cited by examiner

*Primary Examiner* — Venkataraman Balasubramanian
(74) *Attorney, Agent, or Firm* — Akerman LLP

(57) ABSTRACT

An integrated process for the synthesis of urea and melamine, wherein: urea is synthesized with a stripping process in a high-pressure synthesis loop comprising a reactor, a stripper and a carbamate condenser, and the urea solution leaving said stripper is sent to a recovery section to produce a concentrated urea product and a recovered carbamate solution; at least part of said urea product is converted to melamine, and the off-gas from the synthesis of melamine are recycled to the urea synthesis by mixing with the gas phase from the stripper and with said recovered carbamate solution, thus forming a mixed flow which is then condensed in said carbamate condenser, and the condensate is eventually directed to the reactor.

14 Claims, 2 Drawing Sheets

PROCESS AND PLANT FOR THE SYNTHESIS OF UREA AND MELAMINE

This application is a national phase of PCT/EP2015/058292, filed Apr. 16, 2015, and claims priority to EP 14166190.0, filed Apr. 28, 2014, the entire contents of both of which are hereby incorporated by reference.

FIELD OF THE INVENTION

The present invention relates to the field of combined urea melamine plants. The invention discloses an improved technique for recovering the off gas released by the synthesis of melamine.

PRIOR ART

In a combined urea melamine plant, urea is synthesized from ammonia and carbon dioxide, and at least a portion of the urea is used to produce melamine.

Urea is synthesized according to:

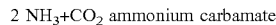

2 $NH_3 + CO_2$ ammonium carbamate

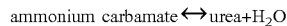

ammonium carbamate $\leftrightarrow$ urea + $H_2O$ while urea is converted into melamine according to:

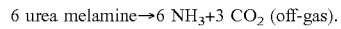

6 urea $\rightarrow$ melamine + 6 $NH_3$ + 3 $CO_2$ (off-gas).

The off gas emerging from the melamine section are usually recycled to the urea section since they contain a relevant amount of the urea reagents, namely ammonia and carbon dioxide.

Melamine can be synthesized with catalytic low-pressure processes or with non-catalytic high-pressure processes. Off gas from a low-pressure melamine process can be recycled to a urea reactor as an aqueous solution which, however, have the drawbacks of low pressure and introduce water in the urea reactor.

The off gas originated by a high pressure melamine process are more suitable for use in the urea synthesis. Referring for example to the stripping urea technology, the melamine off gas are usually recycled to the urea synthesis by introducing them in the high-pressure carbamate condenser of the urea synthesis loop, where they are condensed together with the gaseous phase emerging from the stripper.

A problem faced by the combined urea-melamine plants, where most of the urea synthesized is used to produce melamine, is the reduced amount of gaseous carbon dioxide available to the reactor. This problem is suffered in particular by the urea plants which operate according to the self-stripping process, and/or when a significant amount of the urea synthesized in the urea section is used to produce melamine.

In fact, gaseous carbon dioxide can be regarded as the heat source of the reactor, because the reaction of carbon dioxide with ammonia (forming the ammonium carbamate) is exothermic and generates the heat required by the endothermic dehydration of carbamate. Since in a combined urea-melamine plant part of the CO2 entering the reactor comes from the off gases of the melamine process, which are already condensed, the actual amount of gaseous CO2 condensing in the reactor is lower. Therefore, the use of the synthesized urea for the production of melamine ultimately leads to urea reactor cooling down, hence to a much lower conversion rate leading to higher energy consumptions and higher capital investment due to equipment of bigger size.

The aim of the invention is to provide a solution to the above problem of less carbon dioxide available to the reactor when a significant portion of the synthesized urea is used to produce melamine. Another aim of the invention is to provide a more efficient way to introduce the melamine off gas from non-catalytic high-pressure synthesis of melamine into a urea synthesis loop.

SUMMARY OF THE INVENTION

The above stated purpose is reached with a process for the combined synthesis of urea and melamine, wherein:

urea is synthesized from ammonia and carbon dioxide with a stripping process, said stripping process including at least the steps of reacting ammonia and carbon dioxide in a reaction section, to form an aqueous solution comprising urea, ammonium carbamate and unconverted ammonia, and treating said solution in a stripping section, obtaining a urea solution and a gas phase containing ammonia and carbon dioxide, and also including a step of condensation in a condensation section;

at least a portion of synthesized urea is used to produce melamine in a tied-in melamine plant, obtaining also a flow of melamine off gas which contain ammonia and carbon dioxide, and said flow of melamine off gas is recycled back to said process for the synthesis of urea, either in a gaseous state or in a liquid state after condensation, the process being characterized in that at least a portion of said gaseous phase obtained from the stripping section is fed directly to said reaction section in a gaseous state.

The urea-containing stream transferred from the urea plant to the melamine plant, for the synthesis of melamine, may be a urea melt or an aqueous urea solution according to different embodiments of the invention. In the latter case, the melamine plant includes an evaporation section to remove water from said solution.

Preferably, a portion of said gaseous phase from the stripping section is fed directly to said reaction section, and a remaining portion of said gaseous phase is sent to said condensation section. In other words, the gas emerging from the stripper is split into at least two portions, and one of said portions is directed to the reaction section, for example at the bottom of a reactor.

The term directly means that the portion of stripper gas is sent to the reaction space without substantial process steps, e.g. without condensation.

The process for the synthesis of urea can be any stripping process including for example the CO2 stripping process, sometimes referred to as the "Stamicarbon" process, and the self-stripping process sometimes referred to as "Snamprogetti" process. A description of the urea stripping processes can be found in the literature, for example in the Ullmann's Encyclopedia of Industrial Chemistry, 5$^{th}$ revision, vol. A27.

The above mentioned reaction section, stripping section and condensation section are part of the so-called high-pressure urea synthesis loop. The pressure in the synthesis loop is for example 150 bar. In some embodiments, said loop comprises also a reactor off-gas scrubber. The synthesis of urea may include also at least one recovery section(s) working at a lower pressure, for recovery of unconverted carbamate and ammonia from the solution leaving the stripper.

The melamine off gas may be recycled in a gaseous state or in a liquid state according to various embodiments. The melamine off gas may be available at a high pressure or medium pressure.

Melamine off gas at high pressure have a pressure which is preferably at least 80 bar, more preferably in the range 80-200 bar and even more preferably around 110 bar. The temperature of said high-pressure melamine off gas is preferably 200 to 250° C., and more preferably around 215° C. In some embodiments, they have a pressure which is slightly below the pressure of the urea synthesis loop; for example high pressure melamine off gas may be at a pressure between 100-120 bar.

Melamine off gas at medium pressure have a pressure which is substantially lower than that of the urea synthesis loop, usually in the range 20-40 bar, and even more preferably around 22 bar. The temperature of said medium pressure melamine off gases is preferably 140 to 170° C. and more preferably around 165° C.

Melamine off gas at a high pressure are preferably recycled in a gaseous state; they may be partially or totally condensed in the above mentioned condensation section of the urea synthesis loop. Melamine off gas at a medium pressure (for example around 20 bar) are preferably condensed with the help of water or dilute carbamate solutions and recycled to the urea synthesis as liquid.

A preferred embodiment of the invention provides that the urea solution leaving the stripping section is further processed in at least one recovery section obtaining a liquid carbamate solution and a concentrated urea solution and at least a portion of said solution is used to produce melamine. More preferably, the melamine off gas are recycled to the synthesis of urea by:

mixing said flow of melamine off gas with a portion of said gas phase from the stripping treatment, and with at least a portion of said liquid carbamate solution coming from said recovery section, thus obtaining a gaseous-liquid mixed flow, condensing said mixed flow in said condensation section, obtaining a condensate, and feeding said condensate to said reaction section.

According to the above embodiment, the gas phase emerging from the stripper is split in two currents. A first current is mixed with the melamine off gas and with recovered carbamate solution thus forming the aforesaid mixed flow; the remaining second current of the gas phase from the stripper is sent to the reaction section.

If the pressure of condensation is slightly lower than the pressure of reaction, a pump may be provided.

Preferred features of the invention are in accordance with the dependent claims.

Another aspect of the invention is a combined plant for the synthesis of urea and melamine, according to the attached claims. Yet another aspect of the invention is a modification of a urea plant adding a melamine plant, according to the claims.

The splitting of the gas phase from the stripper has numerous advantages. A first advantage is that the splitting can be regulated in such a way to send the reactor only the amount of vapors necessary to the heat balance, the remaining part of the vapors being mixed with the melamine off gas and recovered carbamate solution, before condensation.

The pressure of the synthesis loop is not dependent on the amount of condensation reached in the loop condenser, and is not dependent on the pressure of the steam generated in the condenser itself.

The inert gases contained in said gas phase are also split between the reactor and the condenser, thus reducing the amount of inert gas in the reactor, which is detrimental to conversion into urea. Given the presence of a lower limit, which corresponds to the amount of oxygen required for the passivation of the reactor, a dedicated air compressor may be introduced if said limit is reached.

The heat contained in the high-pressure melamine off gas can be efficiently recovered during the condensation process. Heat can be recovered, for example, by producing steam. In some embodiments, the production of steam for both the urea section and the melamine section is concentrated in a single equipment (that is in the high pressure condenser of the urea loop), thus reducing the cost and complication of the steam lines.

Mixing the recovered liquid carbamate solution to the melamine off gas helps condensation of gaseous ammonia and carbon dioxide, and reduces the crystallization temperature of the carbamate solution, reducing the risk of precipitation of carbamate. Another advantage is the condensation producing a carbamate solution at a high-pressure and high temperature and substantially free of water. Said carbamate solution can be recycled to the reaction stage, e.g. to a reactor, without expensive pumping and without introducing water into the reactor.

These and other advantages of the invention will appear more evident with the help of the following description of preferred embodiments.

DESCRIPTION OF PREFERRED EMBODIMENTS

Figure 1:
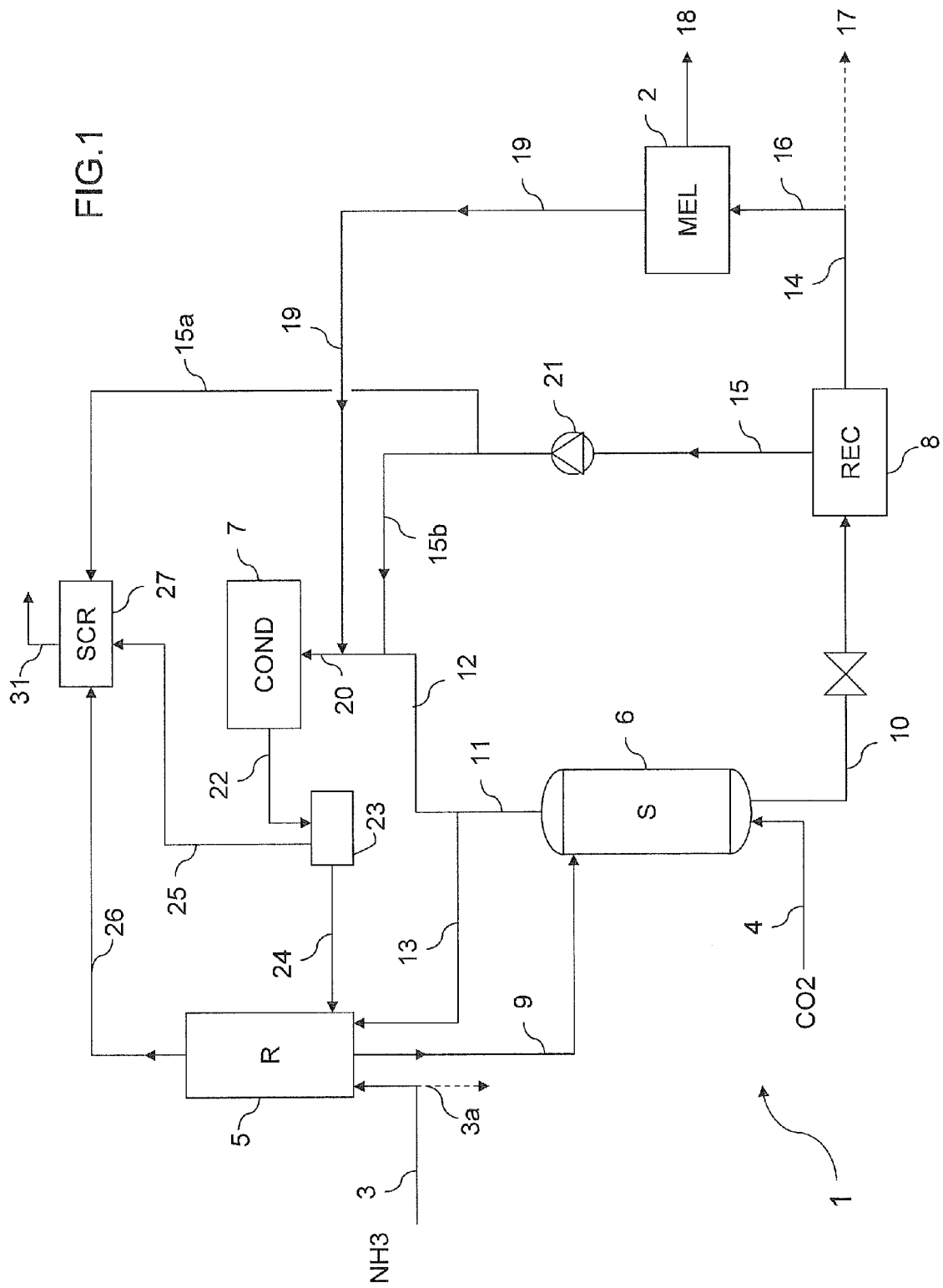
FIG. 1 is a simplified block scheme of a urea-melamine plant according to a first embodiment of the invention, with a urea section operating according to the CO2-stripping process.

FIG. 1 is a general scheme of a plant for the synthesis of urea and melamine. The plant comprises a urea section which is generally denoted by 1, and a melamine section denoted by block 2.

In the urea section 1, urea is synthesized from ammonia input 3 and carbon dioxide input 4. The urea section 1 produces a urea-containing stream in the form of a concentrated aqueous solution 14. At least a portion 16 of said urea solution 14 is used in the melamine section 2 to produce a melamine product 18. A remaining portion 17 may be exported in some embodiments, or sent to a finishing section for the production of a solid urea product. The melamine section 2 includes an evaporation section suitable for bringing the input solution 16 to the desired purity.

The melamine section 2 releases melamine off gas 19 which are recycled back to the urea section 1.

The urea section 1 operates with a stripping process. More in detail, said section 1 comprises a high-pressure loop which includes a reactor 5, a stripper 6, a condenser 7 and possibly a high-pressure scrubber 27. Preferably the stripper 6, the condenser 7 and the scrubber 27 are shell-and-tube heat exchangers. The urea section 1, more preferably, comprises at least one recovery section 8 operating at a pressure lower than pressure of said loop, for example a medium pressure recovery section and/or a low-pressure recovery section.

According to the invention, a portion 13 of the gaseous phase 11 emerging from the stripper 6 is fed directly to the reactor 5. The amount of gaseous carbon dioxide fed to the reactor 5 is regulated in such a way to obtain the desired heat balance, i.e. to provide at least the necessary heat for dehydration of carbamate. In particular, the amount of said portion 13 depends on the amount of urea which is used for the synthesis of melamine compared to the total urea which is synthesized, for example in FIG. 1 the amount of the gaseous portion 13 will depend on the amount of solution 14 directed to the melamine section (line 16). In some embodiments, the portion 16 directed to the melamine block 2 is at least 50% or all of the solution 14.

The synthesis of melamine requires urea of a high purity, typically 99.7%. Referring to the example of FIG. 1 said purity may be reached by subjecting the stream 16 to evaporation. In other embodiments, a high purity urea melt obtained in the urea section and suitable for the synthesis of melamine may be directed to the melamine section.

FIG. 1 illustrates a preferred embodiment with a $CO_2$ stripping urea process, were gaseous carbon dioxide input 4 is fed to the bottom of said stripper 6.

Referring more specifically to FIG. 1, ammonia is directly fed to the reactor 5, while the CO2 feed reaches the reactor 5, after being used in the stripper 6. Optionally, a part of ammonia 3a, instead of being fed to the reactor 5, is sent to the condenser 7. The effluent 9 of the reactor 5 is an aqueous solution of urea containing some carbamate and unconverted ammonia. Said effluent 9 is fed to the stripper 6 for decomposition of the unreacted ammonium carbamate and stripping of ammonia, producing a stripped solution of urea 10 and a gas phase 11 containing ammonia and carbon dioxide. Stripping of the solution 9 is promoted by the feed of gaseous carbon dioxide 4, and heat is furnished for example by hot steam admitted into the shell side of the stripper 6.

A first portion 12 of said gas phase 11 is directed to the condenser 7 and a remaining second portion 13 of said gaseous phase 11 is directed to the reactor 5. The first portion 12, before admission into the condenser 7, is mixed with the off gas 19 coming from the melamine section 2, and with a liquid carbamate solution 15b coming from the recovery section 8.

The recovery section 8 produces the urea product 14, which is urea solution to be concentrated depending on its use, and a liquid carbamate solution 15. The liquid carbamate solution 15 is preferably at a medium pressure, for example being produced in a medium-pressure condenser of said section 8. Preferably, most of the effluent 15 from the recovery section 8, indicated with 15a, is fed directly to the scrubber 27, while the remaining portion 15b, which is less than 50%, is mixed with said first portion 12 of the gas phase 11 from the stripper 6.

The melamine section 2 operates preferably according to the non-catalytic high pressure melamine process.

The melamine section 2 produces the melamine product 18 and the current of off-gas 19 containing ammonia and carbon dioxide.

In the embodiment of FIG. 1, said current 19 is discharged by the melamine section 2 at a high pressure, preferably around 110 bar, and is substantially free of water. Accordingly, the off gas can be introduced in the condenser 7 of the urea synthesis loop.

More preferably, said current 19 is mixed with the first portion 12 of the gas phase 11 emerging from the stripper 6, and also with at least a portion of the liquid carbamate solution 15, namely 15b. The pressure of the carbamate solution 15, to this purpose, is raised with a pump 21. The remaining portion 15a is preferably sent to the scrubber 27 in order to condense vapors from the reactor 5 and receiver 23.

Mixing of the off gas current 19 with said solution 15b and said gas 12 forms a two-phase mixed flow 20 which is admitted to the condenser 7. Mixing the off gas 19 with the liquid carbamate solution 15b has the double advantage of a better condensation of vapors and reduced precipitation of carbamate in the condenser 7.

The condensate flow 22 from said condenser 7 is recycled to the reactor 5, preferably via the carbamate receiver 23. Said carbamate receiver 23 separates a liquid carbamate solution 24 and a gas phase 25 containing non-condensed gas and inerts. The liquid solution 24 is pumped to the reactor 5; the gas phase 25 is sent to the high pressure scrubber 27 for further condensation together with the overhead vapors 26 of the reactor 5. Inerts 31 are vented from the scrubber 27.

Preferably, the condensation process in the condenser 7 is a total condensation, which means that the inlet gases are fully condensed, apart from the unavoidable small fraction of non-condensed gas and inert gas, i.e. the condensate flow 22 is liquid.

The heat content of the currents 19 and 12 can be recovered for example by producing hot steam in the shell side of the condenser 7.

The invention reaches the above stated aims. The current 19 of melamine off gas is recycled to the urea synthesis section in an efficient manner, reducing the consumptions of fresh reagents and the consumption of energy. The CO2-containing gaseous feed 13 directed to the reactor prevents the cooling down of the reactor 5 even if all of the urea solution 14 is used to produce melamine.

Figure 2:
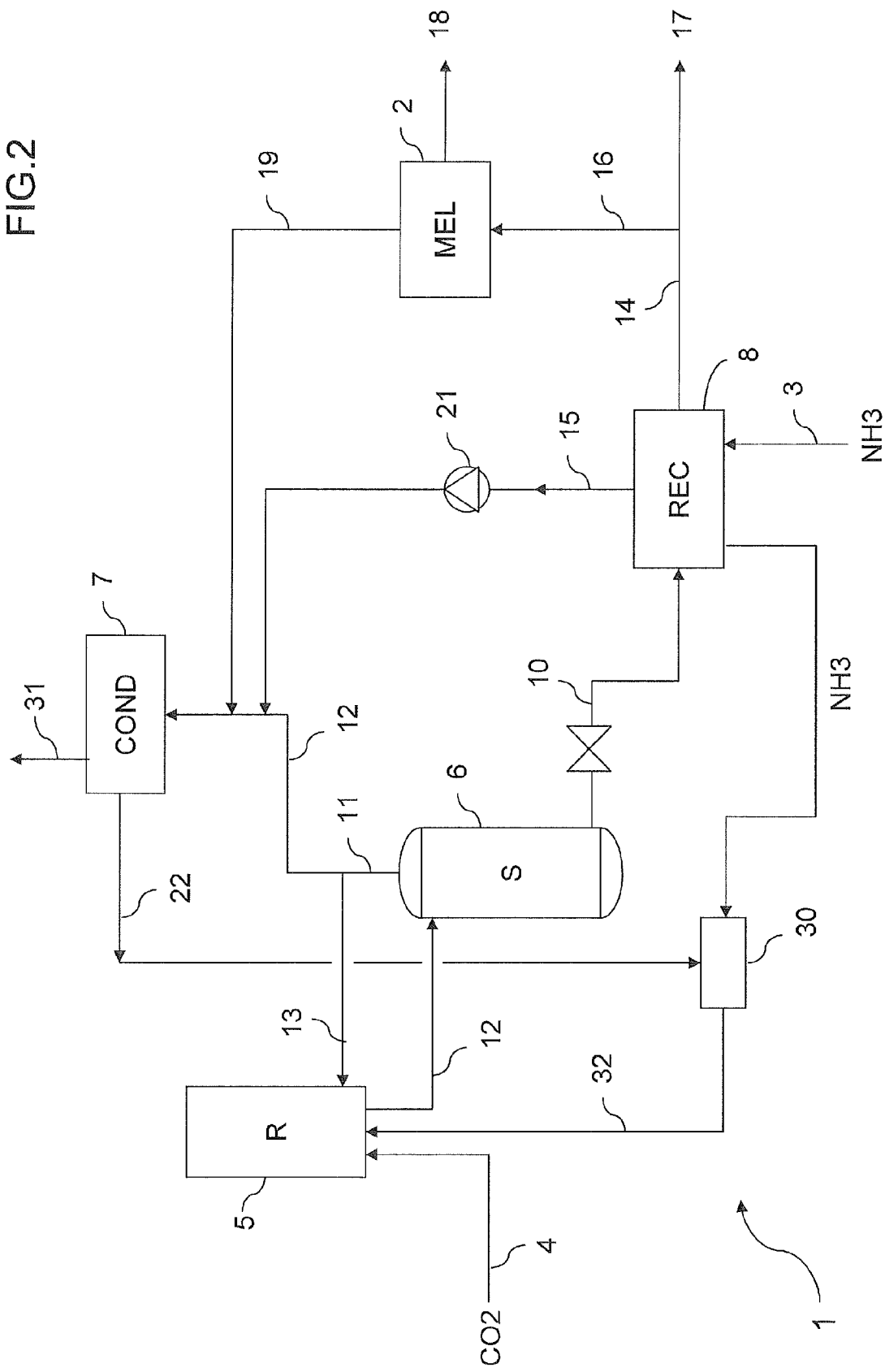
FIG. 2 is is a simplified block scheme of a urea-melamine plant according to a second embodiment of the invention, with a urea section operating according to the ammonia-stripping or self-stripping process.

In the embodiment of FIG. 2, the references have the same meaning as in FIG. 1 and are not explained in detail. However, in this case the CO2 feed 4 is directed to the reactor 5, while the NH3 feed 3 enters the recovery section 8 and reaches the reactor 5 by means of ejector 30. More in detail, the condensate flow 22 from the condenser 7 is recycled to the reactor 5 by means of said ejector 30, forming the reactor input stream 32. Line 31 denotes the inert gas which are vented from said condenser 7.

Also in this embodiment, the gas phase 11 emerging from the stripper 6 is split into two currents, namely a first current 12 directed to the condenser 7 and a second current 13 is fed directly to the reactor 5.

A further aspect of the invention is modification of a urea plant operating according to a stripping process, said urea plant including at least a reactor and a stripper. Said urea plant may run for example the self-stripping process or the CO2 stripping process.

The modification includes adding a tied-in melamine plant which converts into melamine a portion of the urea synthesized by said urea plant. Preferably a major portion and more preferably all of the urea can be used to produce melamine. The off gas of said melamine plant to the urea plant are recycled to the urea plant, and a portion of the gaseous phase separated in the stripper of the urea plant, containing ammonia and carbon dioxide, are directed to the reactor.

The invention claimed is:

1. A process for the combined synthesis of urea and melamine, wherein:
   urea is synthesized from ammonia and carbon dioxide with a stripping process, said stripping process including at least the steps of reacting ammonia and carbon dioxide in a reaction section, to form an aqueous solution comprising urea, ammonium carbamate and unconverted ammonia, and treating said solution in a stripping section, obtaining a urea solution and a gas phase containing ammonia and carbon dioxide, also including a step of condensation in a condensation section, at least a portion of synthesized urea is used to produce melamine in a tied-in melamine plant, obtaining also a flow of melamine off gas which contain ammonia and carbon dioxide, and said flow of melamine off gas is recycled back to said process for the synthesis of urea, either in a gaseous state or in a liquid state after condensation, wherein a first portion of said gaseous phase obtained from the stripping process is fed directly to said reaction section in a gaseous state, and wherein said urea solution leaving the stripping section is further processed in at least one recovery section obtaining a liquid carbamate solution and a more concentrated solution, and a first portion of said concentrated solution is used to produce melamine, and wherein the melamine off gas are recycled to the process for synthesis of urea by:

mixing said flow of melamine off gas with a second portion of said gaseous phase from the stripping treatment, and with a second portion of said liquid carbamate solution coming from said recovery section, thus obtaining a gaseous-liquid mixed flow, condensing said mixed flow in said condensation section, obtaining a condensate, and feeding said condensate to said reaction section.

2. The process according to claim 1, wherein a portion of said gaseous phase from the stripping section is fed directly to said reaction section, and a remaining portion of said gaseous phase is sent to said condensation section.

3. The process according to claim 1, wherein said condensate is further separated into a gaseous phase comprising vapors and non-condensable inert gases and a liquid phase, said gas phase is directed to a process of scrubbing and further condensation, and said liquid phase is fed to said reaction section.

4. The process according to claim 1, said flow of melamine off gas having a pressure of 80 bar or greater, and being substantially free of water.

5. The process according to claim 1, said flow of melamine off gas being released at a medium pressure of no more than 30 bar, and said off gas being recycled to the urea synthesis in a liquid state after condensation.

6. The process according to claim 1, said stripping process for the synthesis of urea being a self-stripping or ammonia stripping process.

7. The process according to claim 1, said stripping process for the synthesis of urea being a CO2-stripping process.

8. The process according to claim 1, wherein the condensation step in said carbamate condensation section is a substantially total condensation.

9. The process according to claim 1, wherein at least 50% of the synthesized urea is used to produce melamine.

10. The process according to claim 9, wherein all the synthesized urea is used to produce melamine.

11. The process according to claim 1, wherein a portion of synthesized urea is used to produce melamine, and a remaining part of the synthesized urea is exported as such or sent to a finishing section.

12. The plant for the synthesis of urea and melamine according to the process of claim 1, the plant comprising a urea synthesis section and a melamine synthesis section, wherein:

said urea synthesis section includes a synthesis loop which in turn comprises at least a reactor, a stripper, and a condenser, the urea section comprises a flow line to feed at least a portion of said gaseous phase leaving said stripper directly to said reactor, and the urea synthesis section comprises at least one recovery section where the urea solution leaving the stripper is further processed, a liquid carbamate solution and a more concentrated urea solution being obtained in said at least one recovery section, said melamine section receives at least a portion of the urea produced in the urea synthesis section, and produces melamine and a flow of melamine off gas containing ammonia and carbon dioxide, the plant comprises flow lines for recycling said flow of melamine off gas back to the urea section, the flow lines arranged to mix said flow of melamine off gas with a first portion of a gaseous phase emerging from said stripper, and with a portion of said liquid carbamate solution coming from said at least one recovery section, thus obtaining a gaseous-liquid mixed flow which is condensed in said condenser of the urea section.

13. A modification of a urea plant operating according to a stripping process, said urea plant including at least a reactor, a stripper and a condenser, the urea plant further comprising at least one recovery section where a urea solution leaving the stripper is further processed, a liquid carbamate solution and a more concentrated urea solution being obtained in said at least one recovery section, and the modification including at least the steps of:

adding a tied-in melamine plant which converts into melamine a portion of the urea synthesized by said urea plant;

recycling the off gas containing ammonia and carbon dioxide withdrawn from of said melamine plant to the urea plant, and directing a first portion of the gaseous phase separated in withdrawn from separated in the stripper of the urea plant, containing ammonia and carbon dioxide, to the reactor of the urea plant, the modification further including:

mixing said off gas withdrawn from the melamine plant with a second portion of said gaseous phase from the stripper, and with a portion of said liquid carbamate solution obtained from said at least one recovery section, thus forming a gaseous-liquid mixed flow which is condensed in said condenser of the urea plant.

14. The process according to claim 1, said flow of melamine off gas being released at a medium pressure of around 20 bar, and said off gas being recycled to the urea synthesis in a liquid state after condensation.

* * * * *